United States Patent [19]

Simon et al.

[11] Patent Number: 4,766,071

[45] Date of Patent: Aug. 23, 1988

[54] PROCESS FOR REGENERATING COENZYMES

[75] Inventors: Helmut Simon, Freising; Alexander Deffner, Garching, both of Fed. Rep. of Germany

[73] Assignee: Henkel Kommanditgesellshaft auf Aktien, Duesseldorf, Fed. Rep. of Germany

[21] Appl. No.: 829,732

[22] Filed: Feb. 14, 1986

[30] Foreign Application Priority Data

Feb. 16, 1985 [DE] Fed. Rep. of Germany ....... 3505397

[51] Int. Cl.$^4$ .................. C12P 19/36; C12P 19/32; C12P 7/40; C12R 1/145
[52] U.S. Cl. ........................................ 435/90; 435/92; 435/136; 435/189; 435/190; 435/842
[58] Field of Search .................. 435/90, 92, 136, 189, 435/190, 842

[56] References Cited

U.S. PATENT DOCUMENTS 4,352,885 10/1982 Zeikuj et al. .................. 435/189

*Primary Examiner*—Lionel M. Shapiro
*Attorney, Agent, or Firm*—Ernest G. Szoke; Henry E. Millson, Jr.

[57] ABSTRACT

The invention relates to a process for the enzymatic preparation or regeneration of coenzymes selected from the group consisting of ATP, acetyl-CoA, acetyl-phosphate, NAD, NADP, NADH, and NADPH from their known oxidized and reduced forms, in which alkanals, such as acetaldehyde, are used as an oxidizing agent or alkanals such as acetaldehyde and alcohols, such as ethanol, are used as a reducing agent and a cell lysate of *Clostridium kluyveri* is used as a biocatalyst.

21 Claims, No Drawings

PROCESS FOR REGENERATING COENZYMES

BACKGROUND OF THE INVENTION

1. Field of the Invention

This invention relates to a process for regenerating, in the presence of a lysate of a microorganism of the species *Clostridium kluyveri*, a number of coenzymes, such as adenosine triphosphate (ATP), acetyl coenzyme A (acetyl-CoA), acetyl phosphate (acetyl-P), oxidized or reduced nicotinamide adenine dinucleotide (NAD or NADH) and oxidized or reduced nicotinamide adenine dinucleotide phosphate (NADP or NADPH), in connection with a biochemical reaction in which the coenzymes are consumed. In this process another agent, either an alcohol or aldehyde, such as ethanol or acetaldehyde also is consumed.

2. Description of Related Art

Due to their ability to function at mild reaction conditions and their high selectivity, enzymes are becoming increasingly more important in chemical engineering applications. However, only relatively few of the enzymes described in the literature have achieved widespread use in industrial processes. Moreover, in only a limited number of examples have enzymes been used which are found only in the interior of cells. Among these latter enzymes are a group of cosubstrate-dependent enzymes which to date, have only been used in scientific investigations. Cosubstrate-dependent enzymes are enzymes which require the presence of certain other substrates in order to catalyze a chemical reaction (the "certain other substrates" are generally referred to as cofactors, coenzymes or cosubstrates). Certain coenzymes are consumed in stoichiometric quantities along with the substrate during the course of the reaction. Examples of these coenzymes are ATP, acetyl-CoA, acetyl-P, NAD(P) and NAD(P)H. Throughout this application, NAD and NADP will be referred to jointly as NAD(P), while their reduced forms, i.e., NADH and NADPH, similarly will be referred to jointly as NAD(P)H.

The significant expense associated with producing large quantities of these coenzymes has effectively precluded their use in the chemical engineering industry. In other words, enzymatic processes employing enzymes that require stoichiometric amounts of a coenzyme for activation generally cannot complete economically with other available synthesis methods.

In order to remedy this situation, attempts have been made to develop procedures for regenerating individual coenzymes. For example, it has been shown that NAD(P) can be converted into NAD(P)H inter alia by allowing the flavoenzymes lipoamide dehydrogenase (EC 1.6.4.3) or ferredoxin reductase (EC 1.6.99.4), or the extracts of certain microorganisms to act on NAD(P) in the presence of reduced methyl viologen (1,1'-dimethyl-4,4-bipyridinium). The reduced methyl viologen can be regenerated by contacting with hydrogen in the presence of hydrogenase or by direct current (See C.-H. Wong et al. *J. Am. Chem. Soc.* 103 (1981), pages 6227–6228 and J. Bader et al. *J. Biotechn.* 1 (1984), pages 95–109).

While these processes significantly reduce the quantity of NAD(P)H needed for an enzymatic reaction, the Wong et al. process is disadvantaged, for example, by its reliance on hydrogen as a reactant and the Bader et al. process is complicated, for example, by the need to employ an electrochemical cell. Similar reactions also have been proposed for regenerating other coenzymes, such as, for example, regenerating acetyl-CoA, acetyl-phosphate or ATP. Unfortunately, the processes require enzymes isolated and purified by complicated methods and/or these processes require the presence of other substrates which themselves are difficult to obtain (G. M. Whitesides, Chi H. Wong, *Aldrichimica Acta* 16 (1983) 27–34).

Accordingly, a need exists in the art of enzyme catalyzed reactions for a simple process for regenerating coenzymes individually or simultaneously in mixtures. An object of the present invention therefore is to provide such a regeneration process which employs alkanols and alkanals containing from 2 to 4 carbon atoms and an enzyme preparation easily obtained by lysis of a cell suspension.

DESCRIPTION OF THE INVENTION

This and other objects are provided by the present invention which in one aspect relates to a process for the enzymatic preparation of, or more appropriately regeneration of the coenzymes adenosine triphosphate (ATP), acetyl coenzyme A (acetyl-CoA), acetylphosphate (acetyl-P), reduced nicotinamide adenine dinucleotide (NaDH) and/or reduced nicotinamide adenine dinucleotide phosphate (NADPH) from their oxidized form wherein the oxidized form of the coenzyme and a primary alkanol and/or alkanal containing from 2 to 4 carbon atoms, are incubated in the presence of a cell lysate of *Clostridum kluyveri*. If desired, other enzymes may also be present.

In another aspect, the present invention relates to the oxidative regeneration, in the presence of the *C. kluyveri* cell lysate, of the coenzymes NAD and NADP, from their reduced forms (NAD(P)H) using alkanals containing from 2 to 4 carbon atoms as the oxidizing agent.

Microorganisms of the species *Clostridium kluyveri* have long been known. They are anaerobic bacteria capable of converting ethanol and acetate into butyrate, caproate and molecular hydrogen. Numerous intracellular enzymes of various strains of this species also have been identified in the scientific literature. For example, R. M. Burton et al. describe the NAD-linked oxidation of acetaldehyde in the presence of coenzyme A to acetyl coenzyme A using a cell-free *C. kluyveri* extract which contains aldehyde dehydrogenase (*J. Biol. Chem.* 202 (1953), page 873–890). R. Lurz (*Arch. Microbiol.* 120 (1979) pages 255–262) describes the isolation of an alcohol-acetaldehyde dehydrogenase complex from *Clostridium kluyveri*. Finally, J. Bader et al. *(Arch Microbiol.* 127 (1980), pages 279–287) describe the hydrogenation of alpha, beta-unsaturated carboxylic acid compounds using a lysate of *Clostridium kluyveri*.

Even though it is well known that *Clostridium kluyveri* has enzymes useful for regenerating certain coenzymes, and although a *Clostridium kluyveri* lysate has been used in certain stereo-selective hydrogenations, it is nevertheless surprising that a lysate of *C. kluyveri*, which has not been subjected to any of the isolation procedures conventionally used to purify enzymes, would show sufficiently stable enzymatic activity to be useful as a biocatalyst for industrial processes. It is similarly surprising that the cell lysate is able to catalyze simultaneously the regeneration of several coenzymes, such as for example ATP, acetyl-CoA, acetylphosphate and NAD(P)H.

Although the reason for the surprising stability of the enzymatic activity of the *C. kluyveri* lysate has not been experimentally substantiated, it is thought that it may be due to a low level of proteases as well as a low level of enzymes which degrade adenosine nucleotides and/or pyridine nucleotides. Thus, lysates of yeast cells of the species *Saccharomyces cerevisiae* or *Candida utilis*, for example, would not be suitable for the process of the present invention, despite the fact that they demonstrate similar enzymatic specificities, because their lysates include a substantial quantity of proteolytic enzymes.

Using the process of the present invention, it is possible to regenerate the coenzymes ATP, acetyl-CoA, acetylphosphate and NAD(P)H with oxidation of an alkanol or alkanal containing from 2 to 4 carbon atoms, particularly ethanol or acetaldehyde. If NAD or NADP is to be regenerated from their reduced form, NAD(P)H, it is necessary to use alkanals, particularly acetaldehyde. In the simultaneous regeneration of several coenzymes and in the regeneration of NAD(P)H from the related oxidized form NAD(P), ethanol preferably is used.

While the present invention can be employed to prepare one or more of the coenzymes (see EXAMPLE 3), it generally is used to regenerate the coenzymes in connection with a particular synthesis. In such cases, the coenzymes present in a reaction mixture are repeatedly regenerated, for example, a few hundred times, during the course of the reaction. Consequently, only small quantities of these coenzymes need be supplied initially to the reaction mixture, e.g., on the order of about 0.1 to 10 mole % based on the substrate consumed in making a desired product.

In simple terms, the regeneration reactions may be illustrated by the following sequence (the solid-line arrows indicate the reactions for regenerating NAD(P)H, acetyl-CoA, acetylphosphate or ATP, while the dashed line arrows indicate the reaction for regenerating NAD(P));

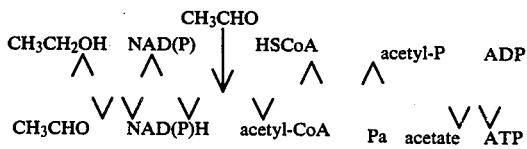

The cell lysate used as a catalyst for regenerating these coenzymes is prepared from a cell culture of a strain of *Clostridium kluyveri*. Suitable strains are, in particular, the strain *Clostridium kluyveri* DSM 555 (Deutsche Sammlung von Mikrooganismen) (ATCC 8527 American Type Culture Collection) and ATCC 12489. The strains DSM 556, 557, 560, 562, 563 and 564 also are suitable. Those skilled in the art will be able to select other suitable strains using routine experimental techniques to test lysates for their ability to regenerate the coenzymes, as for example is described in the following Examples. In order to be suitable, a lysate should exhibit an activity based on enzyme units (U) of at least 20% and preferably an activity of at least 60% of the activity obtained with the strain DSM 555. The unit U is defined such that 1 U of an enzyme catalyzes the reaction of 1 μmole of substrate per minute under optimum physiological conditions.

To obtain the cell lysate used in the process of the present invention, a culture of a strain of *Clostridium kluyveri* initially is prepared in a known manner under anaerobic conditions (i.e. in the absence of oxygen).

Any of the media known from the literature may be used, including for example the medium described by Stadtman et al. (in: *Methods in Enzymology*, Vol. 1, S. P. Colowick, N. O. Kaplan, Eds., pp. 518–523, New York; Academic Press (1955)). Other suitable media are those described by J. Bader et al. in Hoppe-Seyler's *Z. Physiol. Chem. Bad.* 359, page 20, according to which 16 ml of ethanol, 7.5 g of sodium acetate, 2.5 g of glacial acetic acid, 150 mg of diammonium hydrogen phosphate, 100 mg of dipotassium hydrogen phosphate, 33 mg of magnesium chloride-6-$H_2O$, 0.6 mg of magnesium sulfate-7-$H_2O$, 40 mg of calcium chloride-2-$H_2O$, 0.4 mg of manganese sulfate-2-$H_2O$, 0.4 mg of iron sulfate-7-$H_2O$, 50 mg of ammonium chloride, 10 mg of ammonium molybdate-4-$H_2O$, 0.04 mg of biotin, 0.8 mg of para-aminobenzoic acid, 1 mg of resazurin, 6 ml of a 50% solution of potassium carbonate and 1 liter of deionized water are used. The culture medium is deoxygenated and inoculated at 37° C. The culture medium may be agitated, e.g. by stirring, during cell growth. Preferably a sterilized, oxygen-free gas, such as nitrogen, is passed through the culture to facilitate the maintenance of anaerobic conditions.

To harvest the cells, the culture preferably is centrifuged. In order to wash the recovered cell mass, it is suspended, under a nitrogen atmosphere, at 0° C. in a 0.05 molar phosphate buffer solution (pH 7) containing 0.14 mole of sodium chloride and 1 mg of resazurin per liter. 10 mg of sodium dithionite per liter also may be added. For further details, see the last-cited literature reference of J. Bader et al.

To prepare a cell lysate, freshly harvested cells or alternatively a cell suspension previously frozen under deep-freezing conditions (temperatures below −10° C.) and then rethawed, is subjected under anaerobic conditions to a treatment in which the cell membranes are lysed. Destruction of the cell membranes is preferably carried out enzymatically. However, mechanical destruction, for example by sonication, also can be used. In certain cases, chemical or physiochemical destruction techniques, for example, the addition of an appropriate surfactant to the suspension, although less preferred, also can be used to rupture the cell membranes. Since cell lysates generally are viscous liquids, on account of the high molecular weight of the DNA present in them, and thus may be unsuitable for many applications, it often is desirable to digest or depolymerize the DNA and reduce the viscosity of the lysate. This preferably is done by adding known DNA-degrading enzymes (DNAses) to the lysate.

To prepare a particularly suitable cell lysate, *C. kluyveri* cells preferably are suspended in a buffer solution, particularly a phosphate buffer solution having a concentration of from about 0.1 to 0.5 mole per liter and a pH in the range of from about 6 to 8 and preferably of around 7. A buffer solution having a pH-value in the range of from about 6.75 to 7.5 is particularly useful. The lytic enzymes used to rupture the cell wall are added to the cell suspension in an amount of from about 5 to 30 mg and preferably in an amount of from about 15 to 20 mg per gram of wet cell material. A commercially available preparation of lysozyme, for example the product Lysozym (hydrochloride) of Boehringer-Mannheim, preferably is used for this purpose, From about 0.5 to 3 mg and preferably from about 1.5 to 2 mg of a commercial DNAse per gram of wet cell material also is added to the cell suspension either during or after the lysozyme treatment.

The lysate is prepared at a temperature within the range of from about 25° to 40° C. and preferably at a temperature of around 37° C., e.g. at temperatures of from 35° to 37° C. The reaction or incubation time required to complete the enzymatic process of cell lysis and the DNAse-mediated DNA degradation is from about 20 to 90 minutes and preferably from about 60 to 80 minutes. If desired, a sonication treatment at 0° C. may be used thereafter in order to free additional enzymes and increase the activity of the lysate. For small quantities, i.e., for example for a lysate based on a one gram sample of wet cells, the sonication treatment time is 2 minutes in a 30 Watt apparatus. In many cases depending for example upon how and when the lysate is to be used, it also is desirable to add an antibiotic to the lysate. For example, 1 milligram of tetacycline or its hydrochloride salt may be added per gram of cell material used to prepare the lysate.

Cell lysates prepared in accordance with these teachings show high enzymatic activity. According to the present invention, the lysate is used to regenerate coenzymes. The regeneration should be carried out under anaerobic conditions, i.e. in the absence of oxygen. For example, ATP may be regenerated from AMP (adenosine monophosphate) in the presence of catalytic quantities of ADP, or preferably may be regenerated directly from ADP (adenosine diphosphate) in the presence of the *C. kluyveri* lysate. Another reaction catalyzed by the *C. kluyveri* lysate is the regeneration of acetyl coenzyme A from, for example, acetaldehyde and coenzyme A. In addition, NADPH and/or NADH may be prepared from NADP and NAD, respectively. Also, NAD(P) may be prepared from NAD(P)H.

By virtue of the properties of the *C. kluyveri* lysate used as a biocatalyst in the present invention, it is possible to carry out simultaneously the regeneration of NAD(P)H and ATP and/or acetyl CoA and/or acetyl phosphate. These coenzymes also may be individually regenerated. If, for example, it only is desired to regenerate ATP, then NAD need only be used in a catalytic quantity, since NADH formed during the process is reoxidized simultaneously to NAD with the formation of ethanol.

As mentioned above, in the regeneration reactions an auxiliary substrate is consumed either as a reducing agent or as an oxidizing agent depending upon the particular regeneration reaction (see the previously illustrated regeneration sequence). An alkanol or an alkanal containing from 2 to 4 carbon atoms is used as the auxiliary substrate. More specifically, an alkanol or an alkanal can be used as a reducing agent for NAD(P) or an alkanal is used as an oxidizing agent for NAD(P)H. Although, in principle, the process may be carried out with n-butanol, n-butanal, n-propanol, and n-propanal, it nevertheless is preferred to use ethanol and/or acetaldehyde as the alkanol or alkanal.

The reducing agents, alkanol and/or alkanal, and the oxidizing agent, alkanal, should be used in a slight stoichiometric excess, based on the amount needed to regenerate the coenzyme. It is preferred to use an excess of the reducing or oxidizing agent of from about 10 to 50 mole % or, if desired, a very large excess of several hundred mole %.

When the process of the present invention is repeated over a relatively long period of time, it is important to ensure that any acids, such as acetic acid, accumulating, for example, as oxidation products do not interfere with the desired course of the reaction. Accordingly, reactions employing the present invention normally are carried out in a buffered solution of a suitable strength, preferably in a buffered solution having a pH of from about 6 to 8 and preferably in the range of from about 6.75 to 7.5. A suitable buffer is a phosphate buffer. Other physiologically compatible buffers will be apparent to those skilled in the art. For example, it is possible to use a buffer based on the sodium salt of morpholino propane sulfonic acid (MOPS), particularly if acetyl-CoA is to be regenerated. Although buffers used on 1-amino-2-hydroxymethyl-1,3-propanediol (TRIS ®) and inorganic acids, such as hydrochloric acid may be used in some cases, it should be noted that they may be unsuitable for some reactions.

The process according to the invention requires only a catalytic amount of the lysate of *Clostridium kluyveri*. Thus, only about 2 to 50 mg and preferably about 20 to 40 mg of lysate protein (as determined by Bradford's method—literature: S. M. Read, D. H Northcote, *Anal. Biochem.* 116 (1981), page 53 et. seq.) need be used, for example, per millimole of coenzyme to be regenerated or product to be formed with coenzyme regeneration in 4 to 7 hours. Larger quantities likely will be needed for longer reaction times.

It also has been found that the activity of the lysate of *Clostridium kluyveri* when used in the present invention to regenerate ATP, is limited by its acetate-kinase activity. Thus, in another embodiment of the present invention, a separate source of acetate-kinase is additionally added with the lysate. For example, from 5 to 30 enzyme units (U) and preferably from 5 to 20 U and most preferably 10 to 15 U of acetate-kinase may be added per millimole ATP to be regenerated or substrate to be phosphorylated with the consumption of ATP, for example, in 4 to 7 hours. Suitable acetate-kinases (EC1.7.2.1) for use in this embodiment of the present invention may be obtained, for example, from *E. coli*, and are commercially available, for example from Boehringer-Mannheim. In addition, as those skilled in the art will recognize, it is possible to use acetate-kinases from any other microorganism, providing the enzymes have the appropriate level of activity.

The process of the present invention may be used broadly for the preparation of the above-noted coenzymes from their oxidized or reduced forms. However, the present invention is of particular advantage when used to continuously regenerate these coenzymes as an adjunct to a biochemical reaction. The present invention makes it possible to use these coenzymes, which typically are difficult to obtain even in catalytic quantities, in reactions in which they are stoichiometrically consumed.

By using the present invention i.e. by using the lysate of *Clostridium kluyveri* and the added oxidizing or reducing agent as required, e.g., ethanol or acetaldehyde, one can continuously and repeatedly regenerate these coenzymes during the reaction. Thus, the coenzyme ATP and/or the coenzymes NAD(P)H may be regenerated 300 times or even far more frequently during a reaction. Unless NAD(P)H also is consumed for the desired ATP-consuming reaction, NAD(P) may be regenerated with formation of ethanol (from acetaldehyde). The same also applies to acetyl-CoA and/or to acetylphosphate either individually or in admixture with the coenzymes mentioned above. In this connection, it has been found that the *C. kluyveri* lysate used in accordance with the present invention functions as an enzyme catalyst, i.e., the lysate is not merely a source of the coenzymes themselves, active solely by virtue of its large concentration of regenerated coenzymes.

Coenzyme dependent reactions are described in the following Examples. These Examples are intended to illustrate more fully the nature of the present invention, without acting as a limitation on its scope, which is defined by the appended claims. The formation of reaction products show that the coenzymes used in catalytic concentrations are continuously regenerated by the added lysate of *Clostridium kluyveri* DSM 555 and ethanol and/or acetaldehyde.

In these examples, the preparation of glucose-6-phosphate was carried out to demonstrate ATP regeneration. The reductive amination of 2-oxoglutarate to glutamate was carried out to demonstrate NADH or NADPH regenerations, while the enzymatic dehydrogenation of glucose-6-phosphate to 6-phosphogluconate or the dehydrogenation of glucose to gluconic acid was carrier out to show the regeneration of NAD(P). Abbreviations normally encountered in the biochemical literature are used.

EXAMPLES

Example 1

Preparation of glucose-6-phosphate (G-6-P)

General set-up and incubation conditions, unless otherwise indicated: temperature-36° C.; nitrogen atmosphere; reaction medium-aqueous 0.3M potassium phosphate solution having a pH of 7; total volume 1 ml; parallel runs in narrow-necked cylindrical bottles sealed by septa in a Warburg shaker. Protein determinations were carried out using Bradford's method.

Incubation was carried out in the potassium phosphate buffer (PPB) having added thereto: HSCoA 0.3 mM; NAD(P) 1.5 mM;[1] ADP 3.0 mM; $MgCl_2$ 2.5 mM; tetracycline 15 μl (1.5 mg/ml); lysate *C. kluyveri* DSM 555 3.2 mg protein (Bradford test); glucose 150 mM; 4 U acetate-kinase (EC 2.7.2.1) (*E. coli*, Bohringer); approximately 4 U hexokinase (EC 2.7.1.1.) (yeast, Bohringer). 30 μl/hr of a solution of 1.78M $CH_3CHO$ in 1M $K_2HPO_4$ were added. The batches also contain 50–60 mM $(NH_4)_2SO_4$ because the two commercial enzyme preparations added to the buffer solution Ak and Hk (acetate-kinase and hexose-kinase) are supplied as crystal suspensions in 3.2M $NH_4SO_4$.

[1]Concentrations based on a uniform batch size are cited instead of quantities.

The result of incubating this mixture, with hourly addition of 45-50 mM of acetaldehyde, is shown in Table 1 by reporting the accumulation of G-6-P. The catalytic quantity of 0.3 mM of HSCoA is regenerated approximately 330 times and the NAD initially supplied is regenerated approximately 67 times in the regeneration of ATP.

TABLE 1

Formation of G-6-P after certain times where NAD or NADP (1.5 mM) is used
Accumulation of G-6-P after certain times where NAD or NADP is used

| Time | G-6-P Accumulation using NAD | G-6-P Accumulation using NADP |
|---|---|---|
| 0 hr | <3 mM | <3 mM |
| 2 hr | 45 mM | 41 mM |
| 3 hr | — | 50 mM |
| 4 hr | 70 mM | 73 mM |
| 5 hr | 75 mM | 77 mM |
| 6 hr | — | 95 mM |
| 7 hr | 103 mM | 100 mM |

Example 2

Preparation of glucose-6-phosphate (G-6-P)

Set-up with continuous addition of substrate ($CH_3CHO$) and general incubation conditions: Reaction volume at start of incubation was 3 ml; the reaction volume at the end of the incubation was 4 ml; temperature—37° C.; nitrogen atmosphere; magnetic stirrer; reaction medium—aqueous PPB 300 mM.

Incubation was carried out in the PPB solution having added thereto: NAD 1.66 mM; ADP 3.33 mM; HSCoA 0.5 mM; $NH_4SO_4$ 85 mM; $MgSO_4$ 10 mM; tetracycline 50 μl (1.5 mg/ml): glucose 350 mM; $CH_3CHO$: 4M $CH_3CHO$ in $K_2HPO_4$ (2M) was added continuously at a rate of flow of 50 μl/hr; Hk (yeast) approximately 40 U (yeast, Boehringer); AK approximately 20 U (*E. coli*, Boehringer); lysate *Clostridium kluyveri* DSM 555: 600 μl-9.72 mg protein in digestion.

After 18.5 hours 195 mM of G-6-P was detected in the batch (using the enzymatic detection method of G. Lang and G. Michal in H. U. Bergmeyer (Ed.), *Meth. der enzy. Analyse*, 3rd Edition, Vol. II, 1283, Verlag Chemie, Weinheim, 1974).

Example 3

Formation of acetyl-CoA

General incubation conditions: temperature—38° C.; nitrogen atmosphere; initial total reaction volume 1 ml; reaction medium—0.1M Mops buffer having a pH of 7.5 (Sigma).

Incubation was carried out in the Mope buffer having added thereto: NAD 1.25 mM; HSCoA 20 mM; lysate *C. kluyveri* DSM 555—3.5 mg protein/ml, (lysozyme digestion in Mops buffer 0.1 molar having a pH of 7.5); $CH_3CHO$: 50 mM (30 μl of a $CH_3CHO$ solution—diluted 1: 10 in Mops, pH 7.5). After 14.5 hours, 19.75 mM (98% yield) of CoA ester was detected (hydroxamic acid test).

Example 4

NADH and NADPH regeneration without simultaneous formation of ATP

In this example, use is made of the following reactions:

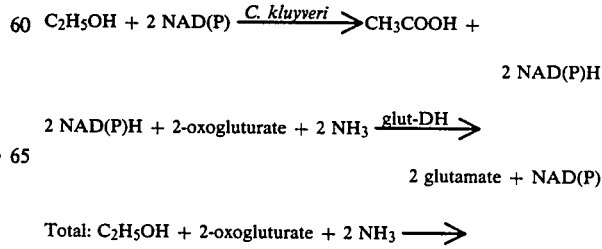

Total: $C_2H_5OH$ + 2-oxogluturate + 2 $NH_3$ ⟶

-continued 2 glutamate + CH₃COOH

The batch contained the following concentrations of components: 300 mM potassium phosphate solution having a pH of 8; 1.5 mM NAD or NADP; 0.3 mM NSCoA; 3.0 mM ADP (to activate the glutamate dehydrogenase); 100 mM 2-oxogluturate; 200 mM ammonium sulfate; 1.2 mM manganese sulfate; 688 mM ethanol; 0.022 mg/ml tetracycline; 15 U glutamate dehydrogenase and lysate of *C. kluyveri* DSM 555, corresponding to 3.5 mg protein.

Under the conditions specified here, there is no need to add coenzyme A (HSCoA). The reaction velocity is the same with or without coenzyme A.

The formation or accumulation of glutamate in the presence of catalytic quantities of NAD is demonstrated in Table 2.

This experiment shows the following: NADH and NADPH may be regenerated by this system. To this end, there is no need for any acetyl-P formed to be split by any addition measures. The catalytic quantities of 1.5 mM NAD (or NADP) are cyclized (i.e., regenerated) 67 times during regeneration of the NADH without any reduction in the activity of the lysate.

TABLE 2

| Formation of glutamate with regeneration of NAD(P)H | | |
|---|---|---|
| Time | Glutamate Accumulation using NAD | Glutamate Accumulation using NADP |
| 0 hr | <2 mM | <2 mM |
| 1 hr | 31 mM | 13 mM |
| 2 hr | 52 mM | 25 mM |
| 3 hr | 70 mM | 34 mM |
| 4 hr | 80 mM | 40 mM |
| 5 hr | −100 mM | 46 mM |

Example 5

Simultaneous regeneration of NAD(P)H and ATP

The results presented in Table 3 demonstrate that ATP and NADH may be simultaneously regenerated. In addition to the additives mentioned in Example 4, this batch contained 100 mM glucose; 15 U hexokinase; 2 mg protein of a crude lysate of *Clostridium sporogenes* ATCC 3584 and, after an incubation interval of 1 hour, 50 mM acetaldehyde were added. Regeneration of NADPH will follow the same course.

| Co-Formation of glutamate and G-6-P with simultaneous regeneration of NADH and ATP | | |
|---|---|---|
| Time | Glutamate | G-6-P |
| 0 hr | <2 mM | <2 mM |
| 1 hr | 49 mM | 17.5 mM |
| 2 hr | 85 mM | 26 mM |
| 3 hr | 85 mM | 26 mM |
| 3 hr | 85 mM | — |
| 5 hr | — | 38 mM |

Example 6

Regeneration of NADP

This regeneration also may be carried out using the system acetaldehyde/crude extract *C. kluyveri*, as confirmed by the following reaction sequence;

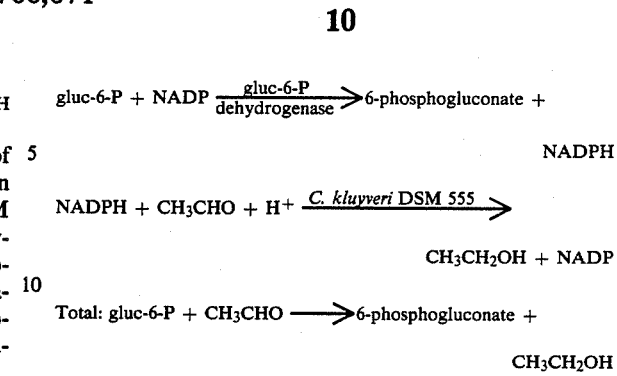

Table 4 demonstrates the dehydrogenation of glucose-6-phosphate by reporting the reduction in G-6-P as a function of time. The batch contained the following concentrations of components: 200 mM potassium phosphate buffer solution having a pH of 7.0; 1.5 mM NADP; 100 mM glucose-6-phosphate; 60 mM acetaldehyde; 2 mg protein/ml (lysate *C. kluyveri*) and 5 U/ml glucose-6-phosphate dehydrogenase. 60 mM of acetaldehyde was added at the start of the incubation and again after one hour of incubation.

TABLE 4

| Removal of G-6-P with regeneration of NADP | | |
|---|---|---|
| Time | G-6-P | Incubation of added CH₃CHO |
| 0 hr | 100 mM | +60 mM |
| ½ hr | 40 mM | — |
| 1 hr | 39 mM | +60 mM |
| 3 hr | 4 mM | — |
| 4 hr | <1 mM | — |

Example 7

Regeneration of NAD:

The regeneration was confirmed by the following reaction sequence:

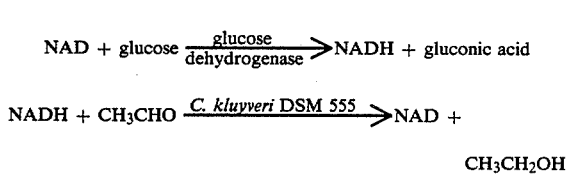

Table 5 shows the dehydrogenation of glucose by reporting the reduction in glucose as a function of time. The following concentrations of components were incubated under suitable conditions: 200 mM potassium phosphate buffer solution having a pH of 7.0; 1 mM NAD; 100 mM glucose; 20 U glucose dehydrogenase (EC 1.1.1.47) (MercK); 2.7 mg protein (lysate *C. kluyveri*); CH₃CHO 53 mM at the start of the incubation and again after ½ hour of incubation.

TABLE 5

| Removal of glucose with simultaneous regeneration of NAD | |
|---|---|
| Time | Glucose |
| 0 hr | 100 mM |
| ½ hr | 40 mM |
| 1 hr | −1 mM |

Although certain specific embodiments of the present invention have been described with particularity herein, it should be recognized that various modifications thereof will be apparent to those skilled in the art.

Therefore, the scope of the present invention is to be limited solely by the scope of the appended claims.

We claim:

1. A process for the enzymatic preparation of a coenzyme selected from the group consisting of adenosine triphosphate, acetyl coenzyme A, acetylphosphate, reduced nicotinamide adenine dinucleotide, reduced nicotinamide adenine dinucleotide phosphate, oxidized nicotinamide adenine dinucleotide, oxidized nicotinamide adenine dinucleotide phosphate, and mixtures thereof from the oxidized or reduced form comprising incubating the oxidized to reduced form of said coenzyme with either a primary alkanol containing from 2 to 4 carbon atoms, a primary alkanal containing from 2 to 4 carbon atoms or a mixture thereof as a reducing agent or a primary alkanal containing from 2 to 4 carbon atoms as an oxidizing agent in the presence of a cell lysate of a microorganism of the species *Clostridium kluyveri*.

2. The process of claim 1 wherein said lysate is obtained by treating a suspension of cells of *C. kluyveri* using a procedure selected from the group consisting of enzyme treatment, mechanical treatment, chemical treatment and a combination thereof.

3. The process of claim 2 wherein said enzyme treatment comprises adding lysozyme to said cell suspension.

4. The process of claim 2 wherein said mechanical treatment comprises sonication.

5. The process of claim 2 wherein said chemical treatment comprises adding surfactant to said cell suspension.

6. The process of claim 2 wherein DNAse is added to the cell lysate to depolymerize DNA.

7. The process of claim 1 wherein said cell lysate is obtained by digesting at a temperature within the range of from about 25° to 40° C. and for a time period of from about 20 to 90 minutes a suspension of freshly harvested cells of a microorganism of the species *Clostridium kluyveri* in a phosphate buffer solution having a concentration of from 0.1 to 0.5 mole per liter at a pH of from 6 to 8 with 5 to 30 mg of lysozyme based on 1 gram of said freshly harvested cells.

8. The process of claim 7 wherein said lysozyme is present in an amount of 15 to 20 mg per gram of said cells.

9. The process of claim 7 wherein said temperature is between 35° to 37°.

10. The process of claim 7 wherein said time period is between 60 to 80 minutes.

11. The process of claim 7 wherein said lysate subsequently is subjected to sonication at a temperature of 0° C.

12. The process of claim 1 wherein the coenzyme comprises a mixture of adenosine triphosphate (ATP) and reduced nicotinamide adenine dinucleotide (NADH).

13. The process of claim 1 wherein the coenzyme comprises a mixture of adenosine triphosphate (ATP) and reduced nicotinamide adenine dinucleotide phosphate (NADPH).

14. The process of claim 12 wherein said coenzyme further includes a member selected from the group consisting of acetyl-phosphate and acetyl-coenzyme A (acetyl-CoA).

15. The process of claim 13 wherein said coenzyme further includes a member selected from the group consisting of acetyl-phosphate and acetyl-coenzyme A (acetyl-CoA).

16. The process of claim 1 wherein NAD(P)H is coverted to NAD(P) with formation of ethanol.

17. The process of claim 1 wherein the alkanol is ethanol and the alkanal is acetaldehyde and the ethanol and acetaldehyde are supplied in stoichiometric excess.

18. The process of claim 1 wherein the microorganism of the species *Clostridium kluyveri* is a strain selected from the group consisting of ATCC 8527, ATCC 12489, DSM 556, DSM 557, DSM 560, DSM 562, DSM 563, DSM 564 and DSM 555.

19. The process of claim 1 wherein the lysate of *Clostridium kluyveri* is used in an amount such that from 2 to 50 mg of lysate protein are present per millimole of coenzyme to be regenerated.

20. The process of claim 1 wherein said incubating is carried out in a buffered solution having a pH of from about 5 to 8 under anaerobic conditions.

21. The process of claim 1 wherein an acetate-kinase is added in an amount of from about 5 to 30 U per millimole of ATP to be regenerated or substrate to be phosphorylated.

* * * * *